US012350128B2

(12) United States Patent
Pratt et al.

(10) Patent No.: US 12,350,128 B2
(45) Date of Patent: Jul. 8, 2025

(54) ADVANCED WOUND DRESSING FOR INCISIONAL WOUNDS THAT PROVIDES APPOSITION FORCES AS A RESULT OF FLUID ABSORPTION

(71) Applicant: Solventum Intellectual Properties Company, Maplewood, MN (US)

(72) Inventors: Benjamin Andrew Pratt, Poole (GB); James Killingworth Seddon, Wimborne (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 567 days.

(21) Appl. No.: 17/639,268

(22) PCT Filed: Aug. 25, 2020

(86) PCT No.: PCT/IB2020/057942
§ 371 (c)(1),
(2) Date: Feb. 28, 2022

(87) PCT Pub. No.: WO2021/038445
PCT Pub. Date: Mar. 4, 2021

(65) Prior Publication Data
US 2022/0331166 A1    Oct. 20, 2022

Related U.S. Application Data

(60) Provisional application No. 62/892,869, filed on Aug. 28, 2019.

(51) Int. Cl.
*A61F 13/0203*    (2024.01)
*A61F 13/00*    (2024.01)

(52) U.S. Cl.
CPC ............ *A61F 13/0203* (2013.01); *A61F 2013/00174* (2013.01)

(58) Field of Classification Search
CPC .... A61F 13/00; A61F 13/02; A61F 13/00008; A61F 13/0203; A61F 13/0209;
(Continued)

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

International Search Report and Written Opinion for Corresponding Application No. PCT/IB2020/057942 mailed Nov. 19, 2020.
(Continued)

*Primary Examiner* — Caitlin A Carreiro (57) ABSTRACT

A dressing for the treatment of incisional wounds includes an upper cover, a patient interface layer, and an absorbent material. The upper cover is configured to substantially cover the incisional wound. The upper cover includes a drape and a plurality of spines coupled to the drape. The drape includes a first side and a second, wound-facing side. The patient interface layer is coupled to the second side of the drape and includes a plurality of openings that are configured to receive fluid from the incisional wound. The absorbent material is disposed between the second side of the drape and the patient interface layer.

20 Claims, 6 Drawing Sheets

(58) Field of Classification Search
CPC ............. A61F 13/0206; A61F 13/022; A61F 13/0226; A61F 13/00021; A61F 13/0243; A61F 2013/00174; A61F 2013/00089; A61F 2013/00246; A61F 2013/00251; A61F 2013/00255; A61F 2013/00582
USPC ............... 602/41–43, 47, 53, 56, 58, 900
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,212,101 B2 * | 7/2012 | Propp ................ A61F 13/0269 602/41 |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0039759 A1 * | 2/2008 | Holm ................ A61F 13/0226 602/41 |
| 2011/0015557 A1 * | 1/2011 | Aali ................ A61F 13/0226 602/56 |
| 2014/0163491 A1 | 6/2014 | Schuessler et al. |
| 2015/0080788 A1 | 3/2015 | Blott et al. |
| 2019/0125590 A1 * | 5/2019 | Rehbein ................ A61F 13/145 |

FOREIGN PATENT DOCUMENTS

| | | |
|---|---|---|
| AU | 755496 B2 | 12/2002 |
| AU | 2009200105 B2 | 4/2015 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |

(56) References Cited

FOREIGN PATENT DOCUMENTS

| | | |
|---|---|---|
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | WO-2005025447 A2 * | 3/2005 .............. A61M 1/80 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

ADVANCED WOUND DRESSING FOR INCISIONAL WOUNDS THAT PROVIDES APPOSITION FORCES AS A RESULT OF FLUID ABSORPTION

CROSS-REFERENCE TO RELATED APPLICATIONS

This application claims the benefit of priority to U.S. Provisional Application No. 62/892,869, filed on Aug. 28, 2019, which is incorporated herein by reference in its entirety.

BACKGROUND

The present disclosure relates generally to wound dressings. More specifically, the present disclosure relates to dressings for the treatment of incisional wounds.

Wound dressings are used to manage wound exudate and fluid levels at the wound site and thereby reduce the risk of infection. In order to capture and retain fluid, some wound dressings include an absorbent material, which swells as it becomes saturated with fluid. This swelling absorbent material tends to apply a downward pressure on the wound, as the absorbent material expands within a gap between the wound and the outer layers of the dressing. This downward pressure/force, directed toward the incisional wound, may interfere with closing of the wound, and thereby inhibit the healing process. It would be desirable to provide an absorbent dressing that provides apposition forces that tend to close the wound as a result of fluid absorption.

SUMMARY

One implementation of the present disclosure is a dressing. The dressing includes an upper cover, a patient interface layer, and an absorbent material. The upper cover is configured to substantially cover the incisional wound. The upper cover includes a drape and a plurality of spines coupled to the drape. The drape includes a first side and a second, wound-facing side. The patient interface layer is coupled to the second side of the drape and includes a plurality of openings that are configured to receive fluid from the incisional wound. The absorbent material is disposed between the second side of the drape and the patient interface layer.

In some embodiments, each of the plurality of spines is configured to be arranged in substantially perpendicular orientation relative to a cut direction of the incisional wound. The plurality of spines may be configured to apply appositional forces to the incisional wound in response to the pressure applied to the drape by the absorbent material. For example, the spines may be arranged in aligned pairs that extend at least partially along a length of the drape. Together, the aligned pairs may define two substantially parallel rows of spines. In some instances, the absorbent material may be approximately centered between the two substantially parallel rows of spines and configured to overlie the incisional wound. The orientation of the absorbent material between the two substantially parallel rows of spines and perpendicular to the orientation of each of the plurality of spines may cause a contraction force to be applied to the incisional wound by the dressing in an appositional direction.

In some embodiments, a capacity of the absorbent material varies across the dressing. For example, the capacity of the absorbent material may be greatest in a region that is approximately centered between the two substantially parallel rows of spines.

In some embodiments, the drape is coupled to the patient interface layer along a perimeter of the drape forming a bonded region. The plurality of spines may be coupled to the second side of the upper cover such that each of the plurality of spines is surrounded by the bonded region.

In some instances, the elasticity of each of the plurality of spines is less than an elasticity of the drape. Each of the plurality of spines may have a thin rectangular shape and may be oriented in a direction that is substantially perpendicular to a longest dimension of the drape. In some instances, each of the plurality of spines is flexible and substantially inelastic (e.g. resistant to stretching).

Another implementation of the present disclosure is a dressing that includes an upper cover, a patient interface layer, and an absorbent material. The upper cover is configured to substantially cover an incisional wound. The upper cover includes a drape having a first side and a second, wound-facing side. The drape defines a plurality of spines. The patient interface layer is coupled to the second side of the drape. The patient interface layer includes a plurality of openings that are configured to receive fluid from the incisional wound. The absorbent material is disposed between the second side of the drape and the patient interface layer.

In some embodiments, the plurality of spines are integrally formed with the drape as a single unitary structure by modifying the drape material properties at the spine locations. For example, the spines may be formed by an ultrasonic welding process applied to the drape.

Another implementation of the present disclosure is a method of making a dressing that includes providing an upper cover having a plurality of spines, providing a patient interface layer having an opening, and providing an absorbent material. The method additionally includes placing the absorbent material onto one of the upper cover and the patient interface layer. The method further includes joining the upper cover and the patient interface layer so that the absorbent material is disposed in between the upper cover and the patient interface layer.

In some embodiments, providing an upper cover includes providing a drape and forming the plurality of spines into the drape by an ultrasonic welding process. The plurality of spines may be arranged in aligned pairs extending at least partially along a length of the upper cover. Together, the aligned pairs may define two substantially parallel rows of spines. In some instances, placing the absorbent material includes joining the absorbent material to the upper cover in a region of the upper cover that is approximately centered between the two substantially parallel rows of spines.

In some embodiments, providing the upper cover includes providing a drape having a first side and a second, wound-facing side, and providing the plurality of spines. Each one of the plurality of spines may include at least one of a felted foam material, a high density foam material, or an injection molded polyurethane material. The method may additionally include joining the plurality of spines to the second side of the drape. In some instances, the patient interface layer may also be coupled to the second side of the drape.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the Figures, a dressing for treating incisional wounds is shown. The dressing is structured to provide appositional forces to the incisional wound in response to swelling of an absorbent material within the dressing to promote wound closure and facilitate healing. The dressing includes a plurality of flexible but substantially inelastic spines coupled to an upper cover of the dressing. The spines (and upper cover) are separated from the incisional wound by an absorbent material, which is configured to absorb wound exudate from the incisional wound. According to an illustrative embodiment, the spines are arranged in substantially perpendicular orientation relative to a lengthwise cut direction of the incisional wound such that the inelastic spines substantially prevent stretching of the upper cover in a perpendicular direction. As the absorbent material swells outwards, away from the incisional wound, the absorbent material presses against the upper cover. The spines, in response to the applied pressure/force from the absorbent material, lift upward and create an appositional force that pulls the edges of the dressing together (e.g. inward in a perpendicular direction toward the incision) to facilitate wound closure and healing.

In some embodiments, the plurality of spines are arranged in aligned pairs that extend at least partially along a length of the drape. Together, the aligned pairs define two substantially parallel rows of spines, which are configured to be separated from one another by the incisional wound. The absorbent material is approximately centered between the two substantially parallel rows of spines and is configured to overlie the incisional wound. As the dressing absorbs wound exudate, the absorbent swells outwardly from the incisional wound. Among other benefits, the arrangement of spines allows for variation in the closure force provided at different positions along the incisional wound. In other words, the spines are configured to work independently or in unison depending on the level of swelling of the absorbent material and exudate locality to substantially prevent excessive closure forces from being applied to regions of the incisional wound that have already closed or are substantially closed (e.g., regions of the incisional wound where lower levels of wound exudate are produced).

In some embodiments, the spines are integrally formed with the drape as a single unitary structure by modifying the material properties at the spine locations. For example, the spines may be formed into the drape using an ultrasonic welding process, which vibrates the drape material at the desired spine locations to modify the material properties and reduce the elasticity of the drape material. Advantageously, integrally forming the spines into the drape minimizes the number of components used in the dressing and the associated manufacturing complexity associated with placing and/or bonding the spines to the drape. These and other features and advantages of the wound therapy system are described in detail below.

Dressing Construction

Figure 1:
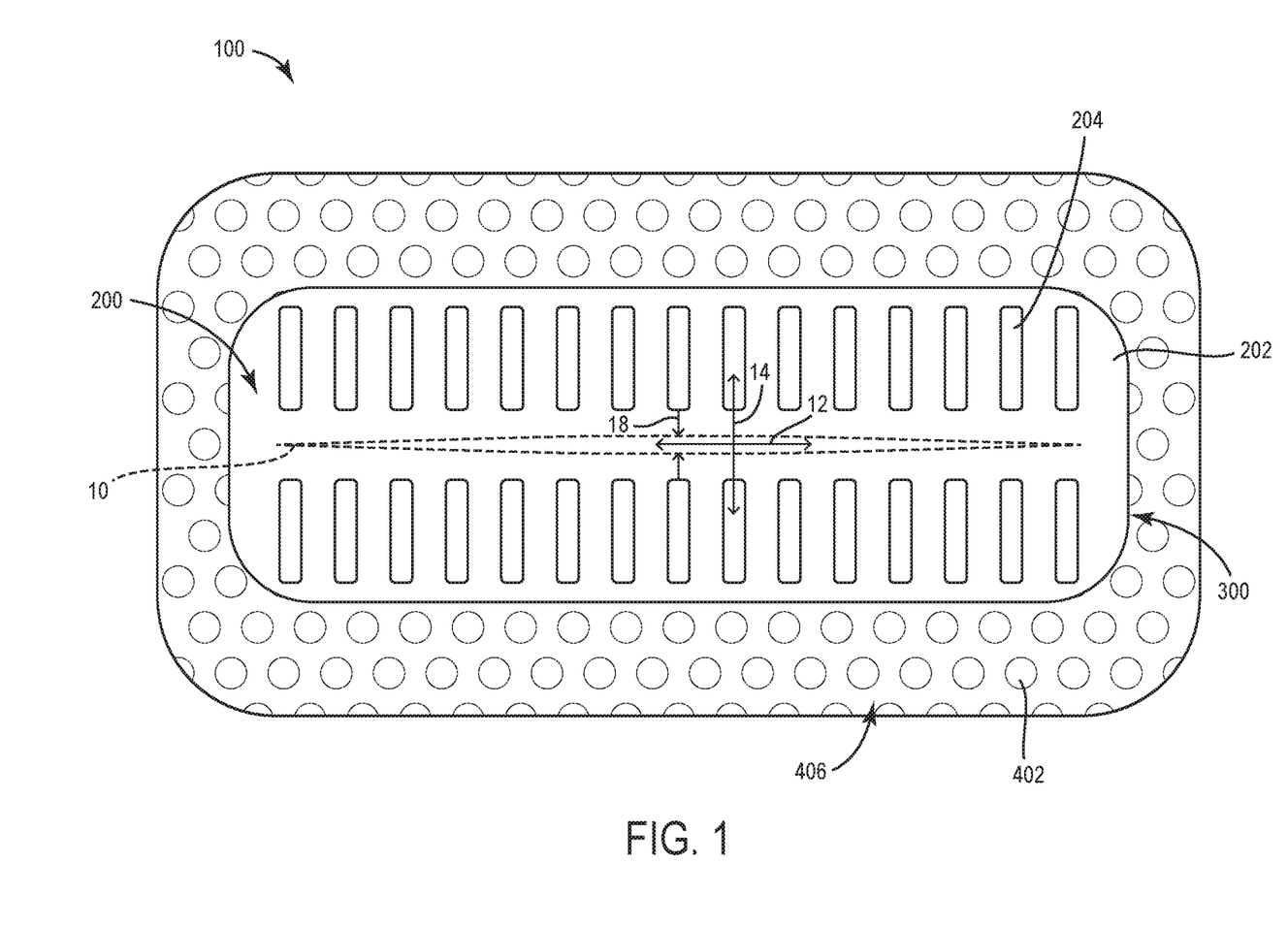
FIG. 1 is a top view of a dressing for treating an incisional wound, according to an illustrative embodiment.

FIG. 1 shows an advanced wound dressing (AWD) 100 applied over an incisional wound, shown as incision 10. The incision 10 may be a cut (e.g., surgical incision, laceration, gash, etc.) in a person's skin or other tissue. The incision 10 extends longitudinally (e.g., horizontally, left to right as shown in FIG. 1) in a cut direction 12. In the illustrative embodiment of FIG. 1, the incision 10 is an elliptical or fusiform shaped excision, which is wide in the middle and tapered at each end. The dressing 100 is disposed centrally over the incision 10 and covers the incision 10. In other embodiments, the dressing 100 may only cover a portion of the incision 10 (e.g., a single leg of the incision, a first portion of an irregularly shaped/non-linear incision, etc.).

Figure 2:
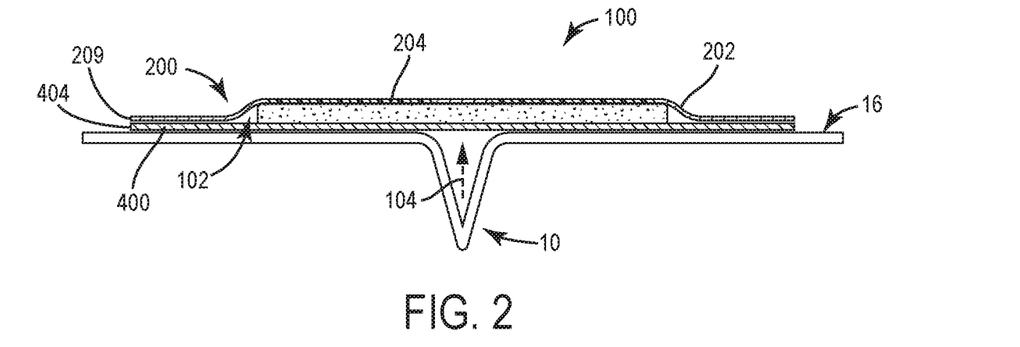
FIG. 2 is a side cross-sectional view of the dressing of FIG. 1 before any fluid has been absorbed by the dressing.
Figure 3:
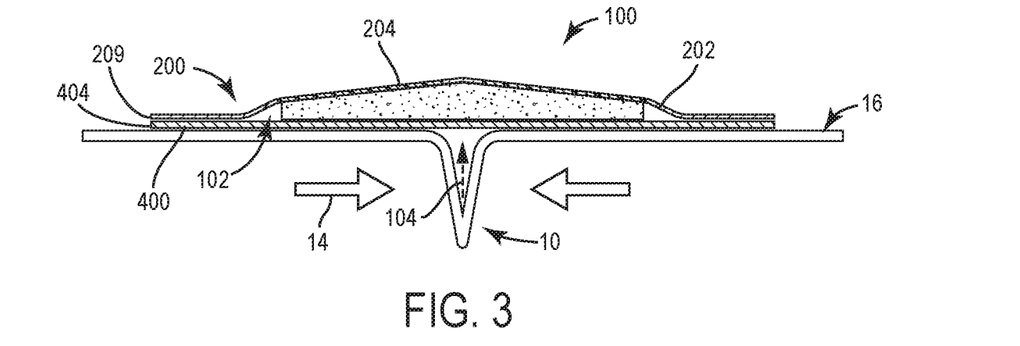
FIG. 3 is a side cross-sectional view of the dressing of FIG. 1 after some fluid has been absorbed by the dressing.
Figure 4:
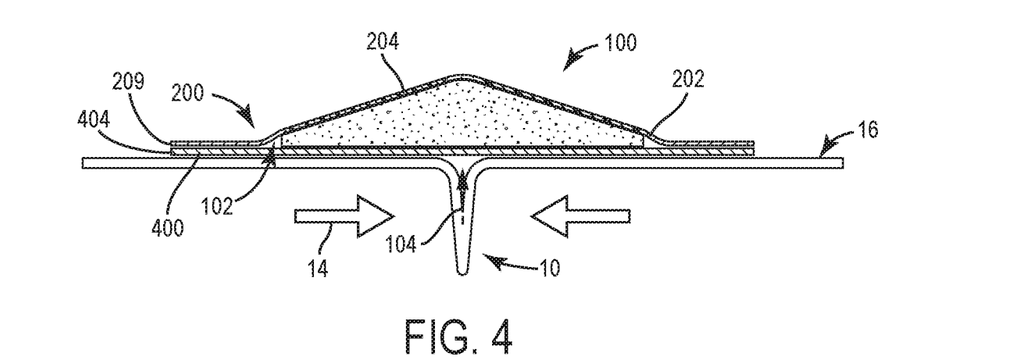
FIG. 4 is a side cross-sectional view of the dressing of FIG. 1 after the dressing has become saturated with fluid.

Referring to FIGS. 2-4, the dressing 100 is shown to include an upper cover 200, an absorbent material 300, and a patient interface layer 400. In other embodiments, the dressing 100 may include additional, fewer, and/or different components. The upper cover 200 extends to an outer edge of the dressing 100 such that the upper cover 200 substantially covers the incision 10 and other parts of the dressing 100. In the illustrative embodiment of FIGS. 2-4, the upper cover 200 is shown to include a drape 202 and a plurality of spines 204. The drape 202 includes a first side 206 and a second, wound-facing side, shown as second side 208. As shown in FIGS. 1-4, each of the plurality of spines 204 is integrally formed with the drape 202 as a single unitary structure. In other embodiments, the spines 204 may be bonded (e.g., adhered) or otherwise coupled to the second side 208 of the drape 202 using glue, epoxy, or another suitable adhesive product. Among other benefits, integrally forming the spines 204 with the drape 202 (or adhering spines 204 to the second side 206 of the drape 202) eliminates the need for additional adhesive products, which might otherwise be required to couple the spines 204 to the first side 206 of the drape 202, to which no adhesive is generally applied. In other words, the spines 204 may be adhered to the drape 202 using an adhesive product that is already pre-applied to the second side 208 for the purpose of bonding the drape 202 to the patient interface layer 400. Moreover, bonding the spines 204 to the second side 208 of the drape 202 shields the spines 204 from an environment surrounding the dressing 100 and prevents the spines 204 from disengaging from the dressing 100. Although there are benefits associated with bonding the spines 204 the second side 208 of the drape 202, the spines 204 may alternatively be coupled to the first side 206 of the drape 202, without significantly impacting wound closure performance.

As shown in FIGS. 2-4, the absorbent material 300 is "sandwiched" or otherwise disposed between the upper cover 200 and the patient interface layer 400. Both the absorbent material 300 and the upper cover 200 are disposed centrally over the patient interface layer 400 and the incision 10. The absorbent material 300 overlies the incision 10 and is configured to absorb and remove wound exudate from the incision 10 (e.g., a wound bed, a wound site, etc.) along a length of the incision 10 in the cut direction 12. The absorbent material 300 may be coupled to at least one of the drape 202 or the patient interface layer 400 in order to substantially prevent movement of the absorbent material 300 relative to the drape 202 and the patient interface layer 400.

As shown in FIGS. 2-4, the patient interface layer 400 is "sandwiched" or otherwise disposed between the absorbent material 300 and an outer surface 16 of a person's skin. The patient interface layer 400 is configured to at least partially seal against the outer surface 16 along a portion of the person's skin or tissue that surrounds the incision 10. As shown in FIG. 1, the patient interface layer 400 includes a plurality of openings 402 configured to fluidly couple the absorbent material 300 to the incision 10. Fluid passing through the openings 402 is received in a cavity 102 formed between the patient interface layer 400 and the drape 202, where the fluid is absorbed by the absorbent material 300. Dashed arrows 104 in FIGS. 2-4 indicate the flow direction of wound exudate entering the cavity 102 from the incision 10. As the absorbent material 300 saturates with fluid, the absorbent material expands (e.g., swells, etc.) to fill the cavity 102.

The patient interface layer 400 is adhered or otherwise coupled to the drape 202 along a perimeter of the patient interface layer 400 in order to substantially prevent fluid communication between the cavity 102 and an environment surrounding the dressing 100, thus protecting both the wound site and any external surfaces from contamination. The drape 202 substantially covers the openings 402 in a bonded region 406 (see FIG. 1) along an outer portion of the patient interface layer 400 (e.g., proximate a perimeter of the patient interface layer 400), which improves adhesion of the dressing 100 to the outer surface 16 of the person's skin. The spines 204 and the absorbent material 300 are surrounded by the bonded region 406. As shown in FIGS. 1-4, the outer dimensions of the drape 202 are similar to the outer dimensions of the patient interface layer 400 such that an outer edge 209 of the drape 202 is approximately flush with an outer edge 404 of the patient interface layer 400. In other embodiments, the drape 202 may extend beyond the outer edge 404 of the patient interface layer 400.

Still referring to FIGS. 2-4, the dressing 100 is configured to provide appositional forces to the incision 10 in response to an applied pressure/force from the absorbent material. As shown in FIG. 1, each of the plurality of spines 204 is arranged to extend in a direction 14 that is substantially perpendicular to a longest dimension of the drape 202 (substantially perpendicular relative to the cut direction 12 of the incision 10) that creates the appositional force. The spines 204 are arranged in substantially aligned pairs that are separated from one another in the appositional direction 14. The spines 204 thus define two substantially parallel rows that straddle the incision 10 and the absorbent material 300. The spacing between spines 204 in each pair may differ in various illustrative embodiments. As shown in FIG. 1, the spines 204 are spaced apart by a distance that is greater than a maximum width 18 of the incision 10. Among other benefits, providing a gap between the spines 204, across the incision 10, provides more room for the absorbent material 300 to swell, reducing the maximum compressive force applied to the incision 10 by the absorbent material 300 while also producing the largest possible appositional forces to draw the incision 10 together. In other embodiments, the spines 204 may extend fully across the incision 10, although in such an arrangement, the therapeutic benefit may not be as significant.

As shown in FIG. 1, the aligned pairs of spines 204 extend along a portion of the drape 202, in the cut direction 12 across the incision 10. Each of the spines 204 has a thin rectangular shape whose longest dimension is oriented substantially perpendicular to the cut direction 12 of the incision 10 (e.g., the appositional direction 14). Each one of the plurality of spines 204 is configured to structurally support the drape 202 and to reduce the compliance of the drape 202 in the appositional direction 14. In other words, each one of the plurality of spines 204 is configured to reduce a maximum amount of deformation (e.g., stretch) of the drape 202 in the appositional direction 14 in response to a force applied to the second side 208 of the drape 202 by the absorbent material 300.

FIGS. 2-4 illustrates the uptake of fluid into the dressing 100 over a period of time, just after the dressing 100 has been applied over the incision 10. As shown in FIG. 2, the drape 202 is sized to engage with the absorbent material 300 in an unsaturated state, before any wound exudate has been absorbed by the absorbent material 300. As shown in FIGS. 2-3, fluid (e.g., wound exudate) passing through the patient interface layer 400 is absorbed by the absorbent material 300, which swells (e.g., increases in volume) to accommodate the fluid within the cavity 102. The swelling absorbent presses outwardly (e.g., upwardly) from the incision 10 toward the second side 208 of the drape 202. The orientation of the absorbent material 300 relative to the spines 204 (e.g., between the two substantially parallel rows of spines 204 along the cut direction 12) causes a contraction force in the appositional direction 14. In other words, the spines 204 resist deformation of the drape 202 in the appositional direction 14, producing a force on the drape 202 and the patient interface layer 400 that promotes closure of the incision 10 locally. As shown in FIGS. 2-3, as the absorbent material 300 continues to expand, the sides of the dressing 100 (e.g., the upper and lower ends of the dressing 100 as shown in FIG. 1) are pulled together by the appositional forces, which effectively closes the incision 10.

It will be appreciated that as the width of the incision 10 decreases, the amount of wound exudate released from the incision 10 will also decrease. Hence, the amount of appositional force applied to the incision 10 may vary along the cut direction 12. For example, the spines 204 may work independently, proximate to a location of a single pair of spines 204 as shown in FIGS. 2-4, or in unison across the incision 10 depending on the amount of swelling of the absorbent material 300 and wound exudate locality. Among other benefits, this ability to vary the appositional force in different regions along the cut direction 12 prevents excessive closure forces from acting upon regions where the incision 10 has already closed (or is substantially closed), thus preventing further deformation of the incision 10 (e.g., puckering, etc.) in regions where healing may be progressing more quickly.

Upper Cover

Figure 5:
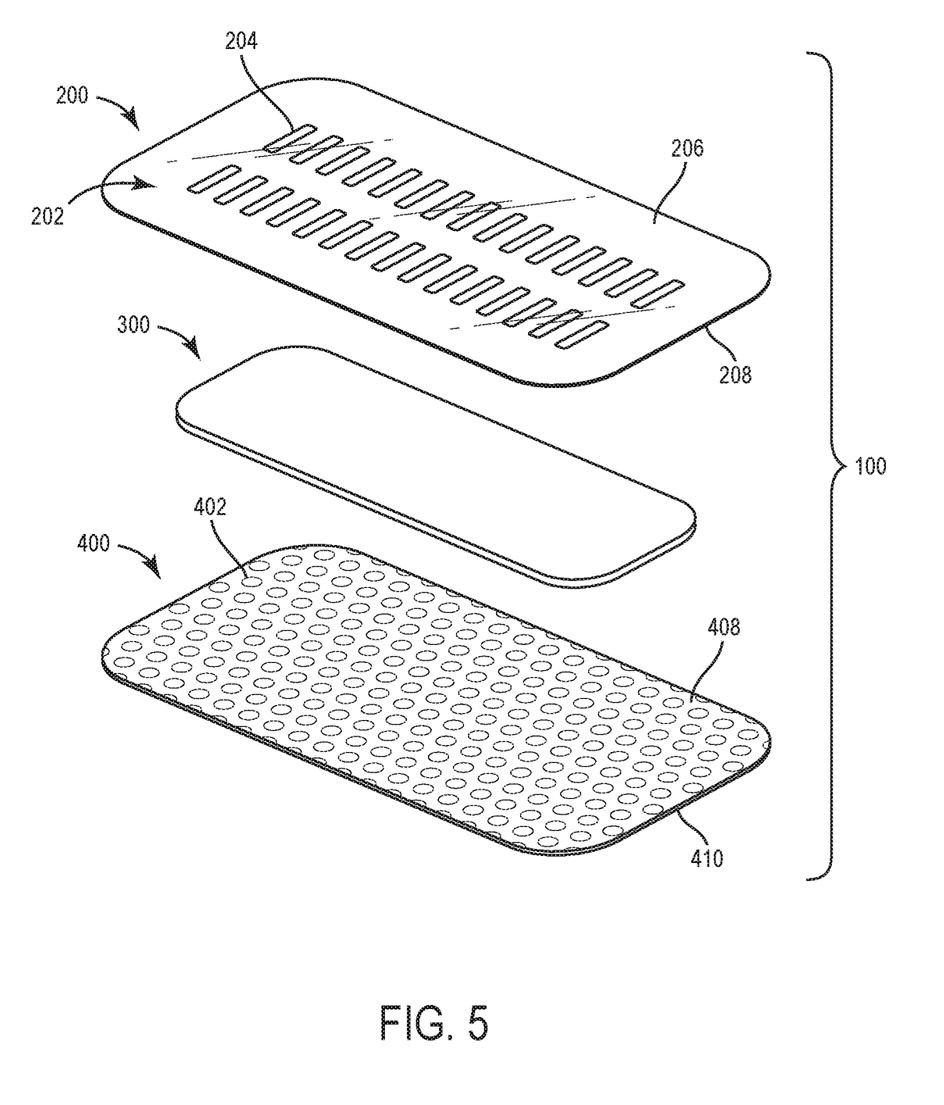
FIG. 5 is an exploded view of the dressing of FIG. 1.

Referring to FIG. 5, an exploded view of the dressing 100 of FIG. 1 is shown, according to an illustrative embodiment. The upper cover 200 is configured to fluidly seal the absorbent material 300 within the dressing 100 to protect both the incision 10 and any external surfaces from contamination. Additionally, the upper cover 200 is configured to position the spines 204 relative to the absorbent material 300. The upper cover 200 includes the drape 202 and the plurality of spines 204. The drape 202 may be made from a thin high moisture vapor transmission rate (MVTR) adhesive coated polyurethane film such as Inspire 2327/2317 or another polyurethane or polyethylene film. The drape 202 may be at least partially coated in adhesive, for example on the second side 208 of the drape 202, in order to bond the drape 202 to at least one of the patient interface layer 400, the spines 204, or the absorbent material 300. Alternatively, the drape 202 may be pattern coated with adhesive so as to increase the MVTR of the dressing 100 (e.g., to improve breathability, to improve the healing effect provided by the dressing 100, to allow at least some of the wound exudate to evaporate from the absorbent material 300 once the absorbent material 300 becomes saturated with wound exudate, etc.).

The spines 204 may be integrally formed or otherwise coupled to the drape 202. In the illustrative embodiment of FIG. 5, the spines 204 are integrally formed with the drape 202 as a single unitary structure by modifying the material properties of the drape 202 at the spine 204 locations. In particular, the material properties are modified such that an elasticity of each of the plurality of spines 204 is less than an elasticity of the drape 202. The change in elasticity of the drape 202 at the spine 204 locations reduces the compliance of the drape 202 in the appositional direction 14 (see also FIG. 1). In some embodiments, the material properties may be modified by heating the drape 202 locally via a suitable forming/heating operation. For example, the spines 204 may be formed into the drape 202 using an ultrasonic welding process that vibrates the material locally in the area of each spine 204. The ultrasonic welding operation reduces the elasticity of the drape 202 in the area of each spine 204 without significantly impacting the flexibility of the drape 202 (i.e., the spines 204 are flexible, but substantially inelastic).

Among other benefits, forming the spines 204 into the drape 202 reduces the number of manufacturing operations required to make the drape 202. In other embodiments, the spines 204 may be formed separately from the drape 202 and may be adhered, bonded, or otherwise coupled to the drape 202. For example, the spines 204 may be made from a felted foam material or high density foam material. In other embodiments, the spines 204 may be made from injection molded polyurethane or another suitably flexible yet substantially inelastic material.

Absorbent Layer

As shown in FIG. 5, the dressing 100 includes an absorbent material 300, layer, or sheet configured to absorb wound exudate and remove it from the incision 10. According to various illustrative embodiments, the absorbent material 300 is made from a superabsorbent laminate such as may be commercially available from Gelok. In other embodiments, the absorbent material 300 includes a printed absorbent polymer.

In some embodiments, absorbent material 300 may be formed from or otherwise include a superabsorbent polymer in the form of granules. The superabsorbent polymer may include Luquasorb 1160 or 1161, such as may be commercially available from BASF. The granules may be contained in a water-soluble carrier polymer. One example of the water-soluble carrier polymer is polyvinylpyrrolidone (PVP). The superabsorbent polymer and the water-soluble polymer may be formed into a slurry or a suspension using an organic solvent. The organic solvent may include propanone or propanol and may aid in delivery of the absorbent material 300 to the drape 202, the patient interface layer 400, or a carrier (e.g., an absorbent foam manifold). In some embodiments, to increase the softness of the superabsorbent granules, a plasticizer may be added to the slurry. In one embodiment, the plasticizer may be water. In some embodiments, the slurry to form the absorbent material 300 may have a formulation of 20 parts by mass of PVP, 10 parts by mass of a superabsorbent polymer, 1 part by mass of glycerol, and 100 parts by mass of propanone. In some embodiments, to plasticize the granules, 1 part to 2 parts by mass of water may be added to the slurry mixture. In other embodiments, a water-soluble polymer superabsorbent precursor, such as acrylic acid or 2-acrylamido-2-methyl-propanesulfonic acid (AMPS), with suitable UV curing additives, may replace the superabsorbent polymer. Such a precursor may be a relatively low viscosity solution and can be printed onto at least one of the drape 202, the patient interface layer 400, or a separate carrier and exposed to UV light to form a soft gel, eliminating the need for a plasticizer. In some embodiments, the water-soluble polymer superabsorbent precursor may be similar to that used for preparing hydrogel coatings.

By way of example, the slurry mixture may be applied to the second side 208 of the drape 202 to form an absorbent layer. In some embodiments, the slurry may be applied to the drape 202 through standard printing methods, such as silk screen printing, gravure printing, or by x-y plotter printing. The absorbent layer may be applied in a variety of different shapes such as circles, squares, hexagons, hoops/halos, stars, crosses, a range of lines, or any combination of shapes. The absorbent layer may be substantially evenly distributed on the drape 202 in a line extending along a central position in between the spines 204. In some embodiments, the absorbent material 300 may include a flexible plasticized hydrophilic polymer matrix having a substantially continuous internal structure. The absorbent material may also be printed or deposited in a particular pattern intended to suit a particular incision and create a desired degree of appositional force for wound closure.

In some embodiments, the absorbent material 300 may include a combination of materials. For example, the absorbent material 300 may include a foam carrier (e.g., GRANUFOAM™ or a closed cell foam material) and a superabsorbent polymer printed in key locations along the foam carrier such that a capacity of the absorbent material 300 varies across the dressing 100 (e.g., varies along the appositional direction 14, etc.). In particular, the superabsorbent polymer may be printed along a line that extends centrally across the foam carrier. In this way, the capacity of the absorbent material 300 will be greatest in a region that is approximately centered between the two substantially parallel rows of spines 204. Among other benefits, increasing the capacity of the absorbent material 300 locally, directly between the two rows of spines 204 may increase the maximum appositional force that can be provided by the dressing 100 to the incision 10.

Patient Interface Layer

The patient interface layer 400 is configured to engage with the patient's skin or tissue to secure the dressing 100 in position over the incision 10. As shown in FIG. 5, the patient interface layer 400 includes an inner surface 408, and an outer, wound-facing surface, shown as outer surface 410. The inner surface 408 is coupled to the second side 208 of the drape 202 proximate to an outer perimeter of the drape 202. The outer surface 410 is coupled to the patient's skin and/or wound bed. The patient interface layer 400 may be made from a polymer film (e.g., polyurethane film) or a medical textile (e.g., Asahi nylon). The patient interface layer 400 may include a suitable low tack adhesive (e.g., silicone or polyurethane gel) to facilitate bonding with the skin surrounding the incision 10. The adhesive may be applied to the outer surface 410 of the patient interface layer 400 proximate to a perimeter of the patient interface layer 400, or at any other suitable location along the outer surface 410. In some embodiments, the adhesive may be distributed evenly across the outer surface 410.

The patient interface layer 400 extends laterally beyond an outer perimeter of the absorbent material 300 and the spines 204. In some embodiments, the patient interface layer 400 may be substantially the same shape and have the same area as the drape 202. As shown in FIG. 5, the patient interface layer 400 includes a plurality of openings 402 configured to receive fluid from the incision 10. The openings 402 include substantially circular holes disposed in a regular pattern across the patient interface layer 400. The size, shape, number, and arrangement of holes may be different in various alternative embodiments. In some embodiments, the openings 402 may be sized and/or shaped to collapse across the incision 10 in order to minimize the resistance of the patient interface layer 400 to the applied appositional forces.

Additional Layers and Configurations

The combination of features shown in the illustrative embodiment of FIGS. 1-5 should not be considered limiting. Many alternative implementations are possible without departing from the inventive concepts disclosed herein. For example, referring to FIG. 6, an advanced wound dressing 500 is shown to include a plurality of spines 504 that are formed separately from the drape 502, according to an illustrative embodiment. The spines 504 are formed together as a single unitary structure, where individual spines 504 are interconnected by narrow webs 506 or strips of spine material (e.g., felted or high density foams, injection molded polyurethane, etc.). The spines 504 are coupled to a second surface of the drape 502 as part of a manufacturing operation when making the dressing 500.

Figure 6:
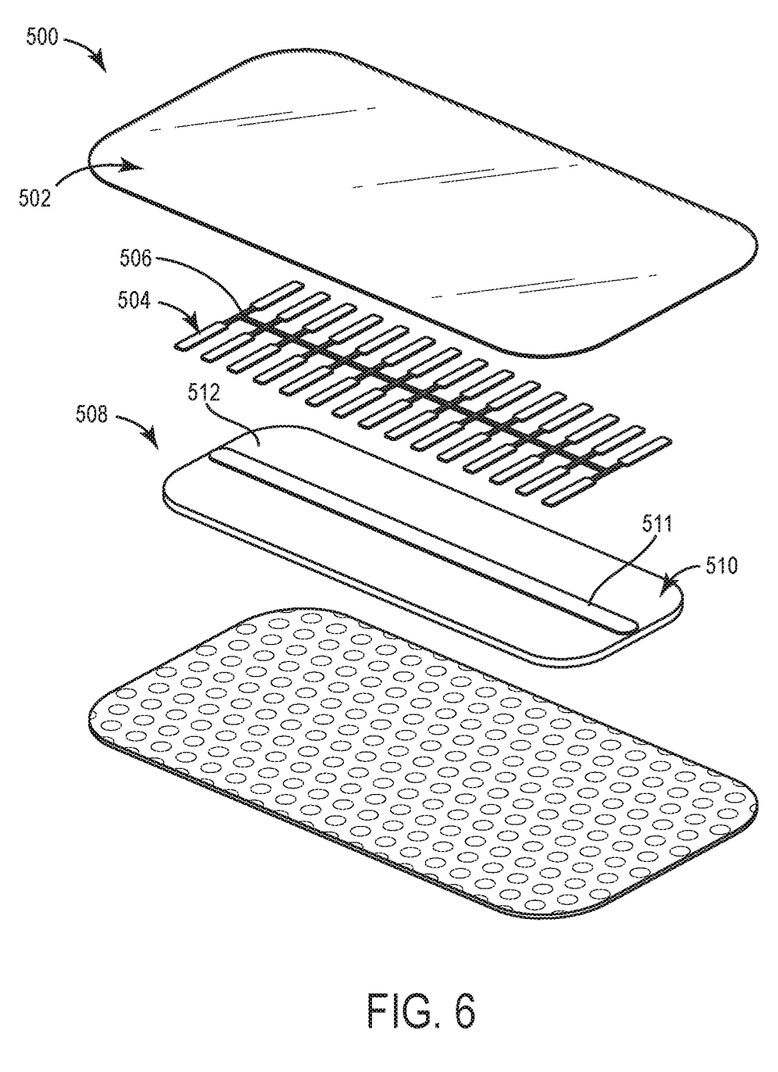
FIG. 6 is an exploded view of a dressing for treating an incisional wound, according to another illustrative embodiment.

Additionally, the dressing 500 of FIG. 6 is shown to include an absorbent layer 508 formed from a combination of superabsorbent materials. The absorbent layer 508 includes a foam carrier 510 and a printed superabsorbent polymer 511. The superabsorbent polymer 511 is printed on an upper surface 512 of the absorbent layer 508, along a line that is configured to be disposed centrally above an incision. Among other benefits, using a carrier for the superabsorbent polymer improves offloading of compression forces across the incision, while also maximizing the appositional forces that can be produced (as a result of preferential swelling of the absorbent above the incision in the area of the superabsorbent polymer).

Method of Making a Dressing for the Treatment of Incisional Wounds

Figure 7:
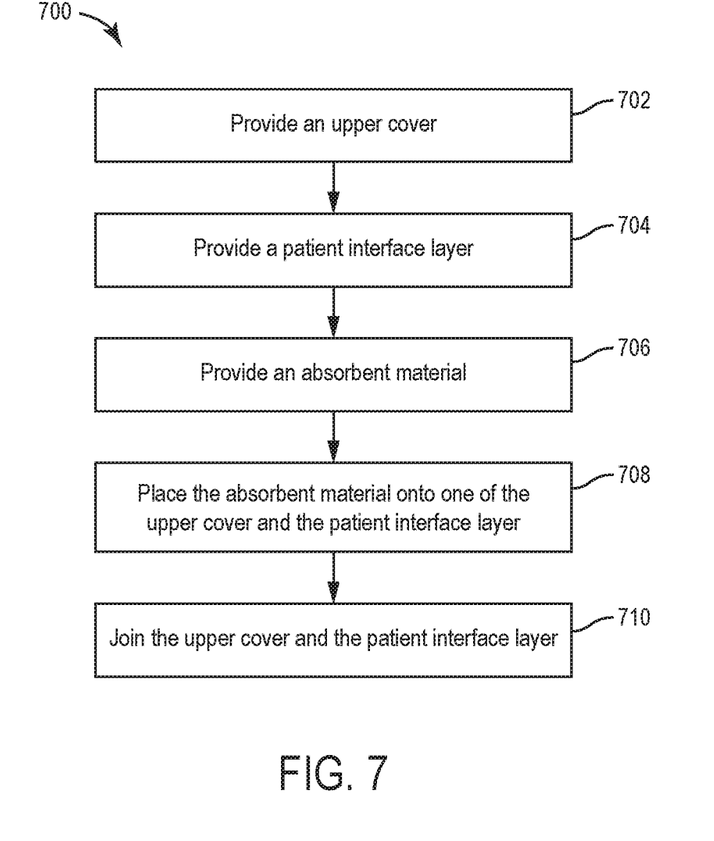
FIG. 7 is a flow diagram of a method of making an incisional wound, according to an illustrative embodiment.

Referring to FIG. 7, a flow diagram of a method 700 of making an advanced wound dressing is shown, according to an illustrative embodiment. The dressing may be the same or similar to the dressing 100, 500 of FIGS. 1-5 and FIG. 6, respectively. For simplicity, similar numbering will be used to identify similar components.

Figure 8:
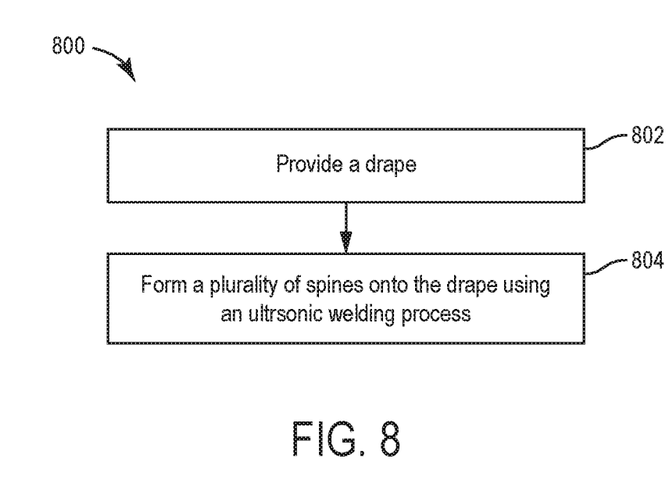
FIG. 8 is a flow diagram of a method of providing an upper cover, according to an illustrative embodiment.
Figure 9:
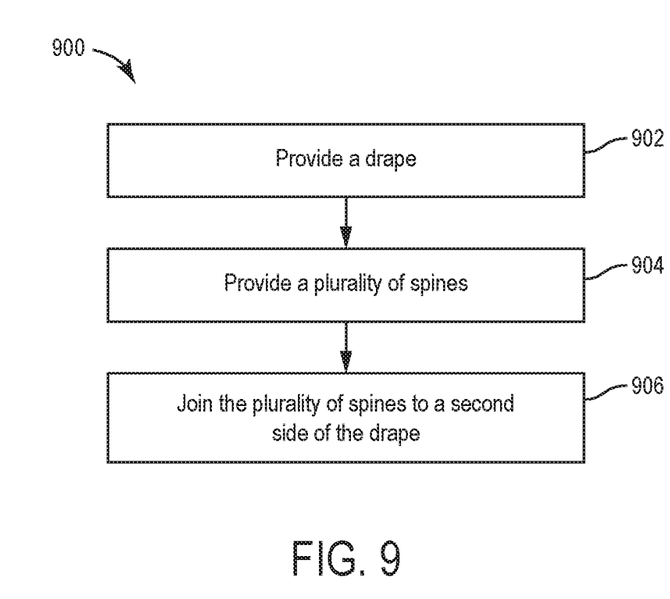
FIG. 9 is a flow diagram of a method of providing an upper cover, according to another illustrative embodiment.

At 702, an upper cover is provided. FIGS. 8-9 show two different methods of providing the upper cover. In the method 800 of FIG. 8, providing the upper cover (e.g., upper cover 200 of FIGS. 1-5) includes providing a drape (e.g., drape 202), at 802. Block 802 may include applying (e.g., spraying, etc.) an adhesive product to one side of the drape to facilitate bonding with other parts of the dressing 100. The method 800 also includes forming a plurality of spines (e.g., spines 204) into the drape by an ultrasonic welding process, at 804. Block 804 may include securing a metal fixture over the drape, in areas of the drape where the material properties are to be altered. Block 804 may additionally include applying a high frequency vibration to the metal fixture in order to reduce the elasticity of the drape, locally, where the metal fixture contacts the drape.

An alternative method 900 of providing the upper cover is shown in FIG. 9. The method 900 includes providing a drape (e.g., drape 502 of FIG. 6), at 902, and providing a plurality of spines (e.g., spines 504), at 904. Block 904 may include forming the plurality of spines via an injection molding process or another suitable forming operation. At 906, the plurality of spines is joined to a second, wound-facing side of the drape. Block 906 may include aligning the spines centrally between outside edges of the drape and adhering the spines to the second side of the drape via glue, epoxy, or another suitable adhesive product.

Returning to FIG. 7, the method 700 of making the dressing further includes providing a patient interface layer (e.g., patient interface layer 400), at 702, and providing an absorbent material (e.g., absorbent material 300), at 704. Block 702 may include perforating a silicone film or sheet to form a plurality of openings, where each opening is configured to receive fluid from an incisional wound. Block 704 may include providing a foam carrier (e.g., foam carrier 510 of FIG. 6) and printing a superabsorbent polymer onto the foam carrier, in a line extending centrally across the foam carrier. Alternatively, or in combination, block 704 may include providing a single superabsorbent material, layer, or sheet.

At 706, the absorbent material is placed onto one of the upper cover and the patient interface layer. Block 706 may include aligning the adhesive material with a gap in between pairs of adjacent spines 204, in a region of the upper cover that is approximately centered between the two substantially parallel rows of spines (see also FIG. 1). Block 706 may further include joining (e.g., bonding, adhering, etc.) a superabsorbent polymer or absorbent sheet to at least one of the drape or the patient interface layer (e.g., via a suitable adhesive product).

At 708, the upper cover is joined together with the patient interface layer. Block 708 may include laminating (e.g., rolling, etc.) the upper cover onto the patient interface layer such that the absorbent material is "sandwiched" or otherwise disposed between the drape and the patient interface layer. The upper cover (e.g., drape) may be bonded to the patient interface layer in a region surrounding the absorbent material. In other embodiments, the method 700 of FIG. 7 may include additional, fewer, and/or different operations.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A dressing, comprising:
    an upper cover configured to substantially cover an incisional wound, the upper cover comprising a drape and a plurality of spines coupled to the drape, the drape having a first side and a second, wound-facing side;
    a patient interface layer coupled to the second, wound-facing side of the drape, the patient interface layer comprising a plurality of openings that are configured to receive fluid from the incisional wound; and
    an absorbent material disposed between the second, wound-facing side of the drape and the patient interface layer;
    wherein at least two of the plurality of spines are configured to be spaced apart by a gap across an incision at the incisional wound and aligned end-to-end substantially perpendicular to a cut direction of the incisional wound to form an aligned pair of spines that extend over the absorbent material.

2. The dressing of claim 1, further comprising a plurality of aligned pairs of spines, wherein at least one aligned pair of spines is configured to be positioned adjacent another aligned pair of spines along the cut direction to define two substantially parallel rows of spines positioned on opposing sides of the gap.

3. The dressing of claim 2, wherein the absorbent material is approximately centered between the two substantially parallel rows of spines and is configured to overlie the incisional wound.

4. The dressing of claim 3, wherein the absorbent material between the two substantially parallel rows of spines and perpendicular to each of the plurality of spines is configured to cause a contraction force only in an appositional direction.

5. The dressing of claim 2, wherein a capacity of the absorbent material varies in different regions of the absorbent material, and wherein the capacity of the absorbent material is greatest in a region that is approximately centered between the two substantially parallel rows of spines.

6. The dressing of claim 1, wherein each of the plurality of spines is configured to be arranged in a substantially perpendicular orientation relative to the cut direction of the incisional wound, and wherein the plurality of spines are configured to apply appositional forces to the incisional wound in response to pressure applied to the drape by the absorbent material.

7. The dressing of claim 1, wherein the drape is coupled to the patient interface layer along a perimeter of the drape forming a bonded region, and wherein each of the plurality of spines is surrounded by the bonded region.

8. The dressing of claim 1, wherein an elasticity of each of the plurality of spines is less than an elasticity of the drape.

9. The dressing of claim 1, wherein each of the plurality of spines is coupled to the second, wound-facing side of the drape.

10. The dressing of claim 1, wherein the plurality of spines are made from at least one of a felted foam material, a high density foam material, or an injection molded polyurethane material.

11. The dressing of claim 1, wherein each of the plurality of spines has a thin rectangular shape.

12. The dressing of claim 1, wherein each of the plurality of spines is oriented in a direction that is substantially perpendicular to a longest dimension of the drape.

13. The dressing of claim 1, wherein each of the plurality of spines is flexible and substantially inelastic.

14. A dressing, comprising:
    an upper cover configured to substantially cover an incisional wound, the upper cover comprising a drape having a first side and a second, wound-facing side, the drape defining a plurality of spines;
    a patient interface layer coupled to the second, wound-facing side of the drape, the patient interface layer comprising a plurality of openings that are configured to receive fluid from the incisional wound; and
    an absorbent material disposed between the second, wound-facing side of the drape and the patient interface layer;
    wherein at least two of the plurality of spines are configured to be spaced apart by a gap across an incision at the incisional wound and aligned end-to-end substantially perpendicular to a cut direction of the incisional wound to form an aligned pair of spines that extend over the absorbent material.

15. The dressing of claim 14, wherein the plurality of spines are integrally formed with the drape as a single unitary structure by modifying the drape material properties at spine locations.

16. The dressing of claim 15, wherein the plurality of spines are formed by an ultrasonic welding process.

17. A method of making a dressing, comprising:
    providing an upper cover comprising a plurality of spines, at least two of the plurality of spines aligned end-to-end and extending substantially perpendicular to a lengthwise dimension of the upper cover to form an aligned pair of spines;
    providing a patient interface layer comprising an opening;
    providing an absorbent material;
    placing the absorbent material onto one of the upper cover and the patient interface layer; and
    joining the upper cover and the patient interface layer, wherein the absorbent material is disposed in between the upper cover and the patient interface layer with the plurality of spines extending over the absorbent material.

18. The method of claim 17, wherein providing the upper cover comprises:
    providing a drape; and
    forming the plurality of spines into the drape by an ultrasonic welding process.

19. The method of claim 17, further comprising a plurality of aligned pairs of spines defining two substantially parallel rows of spines, and wherein placing the absorbent material comprises:
    joining the absorbent material to the upper cover in a region of the upper cover that is approximately centered between the two substantially parallel rows of spines.

20. The method of claim 17, wherein providing the upper cover comprises:
- providing a drape having a first side and a second, wound-facing side;
- providing the plurality of spines, each one of the plurality of spines comprising at least one of a felted foam material, a high density foam material, or an injection molded polyurethane material; and
- joining the plurality of spines to the second, wound-facing side the drape, and wherein the patient interface layer is also coupled to the second, wound-facing side of the drape.

\* \* \* \* \*